(12) United States Patent
Funamoto et al.

(10) Patent No.: US 10,731,200 B2
(45) Date of Patent: Aug. 4, 2020

(54) QUANTIFICATION METHOD FOR AMMONIA, QUANTIFICATION REAGENT KIT, TEST PIECE, AND AMMONIA QUANTIFICATION DEVICE

(71) Applicant: ARKRAY, Inc., Kyoto (JP)

(72) Inventors: Takehiro Funamoto, Kyoto (JP); Masaki Murakami, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 106 days.

(21) Appl. No.: 15/788,076

(22) Filed: Oct. 19, 2017

(65) Prior Publication Data
US 2018/0112250 A1    Apr. 26, 2018

(30) Foreign Application Priority Data

Oct. 25, 2016 (JP) .................. 2016-208760
Jun. 15, 2017 (JP) .................. 2017-118045

(51) Int. Cl.
| | | |
|---|---|---|
| *C12Q 1/32* | (2006.01) | |
| *C12Q 1/25* | (2006.01) | |
| *C12Q 1/48* | (2006.01) | |
| *C12Q 1/54* | (2006.01) | |

(52) U.S. Cl.
CPC .................. *C12Q 1/32* (2013.01); *C12Q 1/25* (2013.01); *C12Q 1/485* (2013.01); *C12Q 1/54* (2013.01); *C12Y 101/01049* (2013.01); *C12Y 603/01002* (2013.01); *G01N 2333/904* (2013.01); *G01N 2333/91215* (2013.01)

(58) Field of Classification Search
None
See application file for complete search history.

(56) References Cited

U.S. PATENT DOCUMENTS 5,916,761 A * 6/1999 Koga ..................... C12Q 1/527
435/15

FOREIGN PATENT DOCUMENTS

| DE | 3621448 A1 | 1/1987 |
|---|---|---|
| EP | 0881301 A1 | 12/1998 |
| JP | S59-198995 A | 11/1984 |
| JP | S62-003800 A | 1/1987 |
| JP | S62-142272 A | 6/1987 |
| JP | 2000-232898 A | 8/2000 |
| JP | 2000-253898 A | 9/2000 |

OTHER PUBLICATIONS

Altman "On the Oxygen-Sensitivity of Various Tetrazolium Salts" Histochemie 22, 256-261 (1970) (Year: 1970).*
Coburn et al. "Improved Manual and Automated Colorimetric Determination of Serum Glucose, with Use of Hexokinase and Glucose-6-Phosphate Dehydrogenase" Clinical Chemistry, vol. 19, No. 1, 1973, pp. 127-130 (Year: 1973).*
Mayer et al. "A Colorimetric Assay to Quantify Dehydrogenase Activity in Crude Cell Lysates" Journal of Biomolecular Screening vol. 7, No. 2, 2002, pp. 135-140 (Year: 2002).*
Extended European Search Report issued in corresponding European Patent Application No. 17197033.8 dated Jan. 8, 2018.

* cited by examiner

*Primary Examiner* — Thane Underdahl
(74) *Attorney, Agent, or Firm* — Morgan, Lewis & Bockius LLP

(57) ABSTRACT

A method of quantifying ammonia, which method includes: performing a first reaction in which a test liquid containing ammonia is reacted with ATP and L-glutamic acid in the presence of glutamine synthetase to produce ADP; performing a second reaction in which the produced ADP is reacted with glucose in the presence of ADP-dependent hexokinase to produce glucose-6-phosphate; performing a third reaction in which the produced glucose-6-phosphate is reacted with an oxidized NAD compound in the presence of glucose-6-phosphate dehydrogenase to produce a reduced NAD compound; and quantifying the reduced NAD compound to quantify ammonia.

10 Claims, 2 Drawing Sheets

QUANTIFICATION METHOD FOR AMMONIA, QUANTIFICATION REAGENT KIT, TEST PIECE, AND AMMONIA QUANTIFICATION DEVICE

CROSS-REFERENCE TO RELATED APPLICATION

This application claims priority under 35 USC 119 from Japanese Patent Application No. 2016-208760 and Japanese Patent Application No. 2017-118045, the disclosure of which is incorporated by reference herein.

All publications, patent applications, and technical standards mentioned in this specification are herein incorporated by reference to the same extent as if each individual publication, patent application, or technical standard was specifically and individually indicated to be incorporated by reference.

TECHNICAL FIELD

The present invention relates to a quantification method for ammonia, a quantification reagent kit, a test piece, and an ammonia quantification device.

BACKGROUND ART

Known examples of methods of quantification of ammonia include chemical measurement methods and enzymatic measurement methods. A chemical measurement method that is mainly used is the indophenol method. Examples of the enzymatic measurement methods include methods using glutamate dehydrogenase, as well as methods using glutamine synthetase, NAD (nicotinamide adenine dinucleotide) synthetase, carbamate kinase, carbamoyl phosphate synthetase, or the like.

Examples of the enzymatic measurement methods using glutamine synthetase that have been proposed include a method in which glutamine synthetase is allowed to act on ammonia, adenosine triphosphate (ATP), and L-glutamic acid, and kinase is allowed to act on the produced adenosine diphosphate (ADP) and a kinase substrate phosphorus compound, followed by quantifying the produced kinase reaction product to quantify ammonia (see, for example, Patent Document 1). More specifically, a method in which pyruvate kinase is allowed to act on the produced ADP and phosphoenolpyruvate to produce pyruvic acid, and pyruvate oxidase is allowed to act on the produced pyruvic acid, followed by quantifying the produced hydrogen peroxide by a peroxidase-based color reaction to quantify ammonia has been proposed.

Other examples of the enzymatic measurement methods using glutamine synthetase that have been proposed include a method of quantifying ammonia in which glutamine synthetase is allowed to act on a test liquid containing ammonia in the presence of ATP and L-glutamic acid which are not the components to be quantified, and purine nucleotide phosphorylase is allowed to act on the produced inorganic phosphate in the presence of purine nucleotides, followed by quantifying a produced purine compound with xanthine oxidase (see, for example, Patent Document 2).

Examples of the enzymatic measurement methods using NAD synthetase that have been proposed include a method in which NAD synthetase is allowed to act on a test liquid in the presence of ATP, deamido-NAD, ammonia as an amide donor, and $Mg^{2+}$, to perform the major reacn, and the NAD produced by the major reaction is subjected to a coenzyme cycling reaction, followed by quantifying a component consumed or produced by the cycling reaction to measure ammonia (see, for example, Patent Document 3).

PRIOR ART DOCUMENTS

Patent Documents

[Patent Document 1] Japanese Patent Application Laid-Open (JP-A) No. S62-3800
[Patent Document 2] JP-A No. S62-142272
[Patent Document 3] JP-A No. S59-198995

SUMMARY OF THE INVENTION

Problems to be Solved by the Invention

In the method of measuring ammonia described in Patent Document 3, a substrate is amplified by the cycling method. Since the reaction proceeds at an accelerated rate even with a small amount of sample, the reaction easily reaches the plateau, and therefore control of the reaction depending on the concentration of the sample is difficult, which is problematic. Moreover, in a case in which an enzymatic reaction is used, the reaction is easily influenced by the measurement temperature and the like. Therefore, in a case in which the measurement environment easily changes, the result of measurement may vary in the cycling method. Furthermore, since the method described in Patent Document 3 uses NAD synthetase, which is very expensive, a method capable of quantifying ammonia at a lower cost is desired.

The methods of quantifying ammonia described in Patent Documents 1 and 2 are methods in which ammonia is quantified by an end-point method. Here, the method described in Patent Document 1 is easily influenced by dissolved oxygen since a color reaction using an oxidase is carried out, which is problematic.

In the method described in Patent Document 1, when pyruvate oxidase is allowed to act on the produced pyruvic acid, phosphoric acid produced upon L-glutamine production and oxygen are used in the reaction to produce acetyl phosphate, carbon dioxide, and hydrogen peroxide. Thus, in the method described in Patent Document 1, phosphoric acid is used as a substrate during the reaction similarly to the method described in Patent Document 2. Since phosphoric acid is a substance that is present in test liquids such as blood (from 2.5 mg/dL to 4.5 mg/dL), urine (from 0.3 g/day to 2.2 g/day), and saliva (about 16.8 mg/dL), the measurement result may have a positive error depending on the phosphoric acid concentration in the test liquid. Thus, a method that enables quantification of ammonia without use of phosphoric acid as a reaction substrate is desired.

An object of the invention is to provide a quantification method for ammonia, a quantification reagent kit, a test piece, and an ammonia quantification device, which enable highly sensitive quantification of ammonia without use of phosphoric acid as a reaction substrate.

Means for Solving the Problems

In the method using glutamine synthetase described in Patent Document 1, ammonia is quantified by a color reaction using an oxidase. Thus, no method using a dehydrogenase has been disclosed so far. As a result of intensive study on a detection system based on a reduction system using glutamine synthetase and then a dehydrogenase, the present inventors succeeded in establishment of a detection system based on a reduction system using a dehydrogenase by using an ADP-dependent hexokinase. That is, in a method using glutamine synthetase, the present inventors completed a novel ammonia detection system based on a reduction system using a dehydrogenase, which is different from conventionally known ammonia detection systems in which an oxidation-based coloring pigment is used together with an oxidase, thereby reaching the invention.

More specifically, the object can be achieved by the following means.

<1> One embodiment of the invention is a method of quantifying ammonia, the method comprising: performing a first reaction in which a test liquid containing ammonia is reacted with ATP and L-glutamic acid in the presence of glutamine synthetase to produce ADP;

performing a second reaction in which the produced ADP is reacted with glucose in the presence of ADP-dependent hexokinase to produce glucose-6-phosphate;

performing a third reaction in which the produced glucose-6-phosphate is reacted with an oxidized NAD compound in the presence of glucose-6-phosphate dehydrogenase to produce a reduced NAD compound; and quantifying the reduced NAD compound to quantify ammonia.

<2> One embodiment of the invention is the method of quantifying ammonia according to <1>, wherein quantifying the reduced NAD compound to quantify ammonia is carried out by quantifying a pigment obtained by reacting the produced reduced NAD compound with a coloring agent.

<3> One embodiment of the invention is the method of quantifying ammonia according to <1> or <2>, wherein the first reaction further includes at least one of a magnesium ion ($Mg^{2+}$) or a manganese ion ($Mn^{2+}$), as a catalyst to produce the ADP.

<4> One embodiment of the invention is a quantification reagent kit, comprising: a first reagent containing glucose; and a second reagent containing glutamine synthetase, ADP-dependent hexokinase, and glucose-6-phosphate dehydrogenase; wherein ATP, L-glutamic acid, and an oxidized NAD compound are each independently contained in at least one of the first reagent or the second reagent.

<5> One embodiment of the invention is the quantification reagent kit according to <4>, wherein ATP, L-glutamic acid, and the oxidized NAD compound are contained in the first reagent.

<6> One embodiment of the invention is the quantification reagent kit according to <4> or <5>, wherein: the first reagent further contains a coloring agent, and the second reagent further contains an electron carrier.

<7> One embodiment of the invention is a test piece, comprising glucose, glutamine synthetase, ADP-dependent hexokinase, glucose-6-phosphate dehydrogenase, ATP, L-glutamic acid, and an oxidized NAD compound.

<8> One embodiment of the invention is an ammonia quantification device, comprising: a reaction section in which a test subject containing ammonia, glucose, glutamine synthetase, ADP-dependent hexokinase, glucose-6-phosphate dehydrogenase, ATP, L-glutamic acid, and an oxidized NAD compound, is arranged, wherein, in the test subject: as a first reaction, the ammonia is reacted with ATP and L-glutamic acid in the presence of glutamine synthetase to produce ADP; as a second reaction, the produced ADP is reacted with glucose in the presence of ADP-dependent hexokinase to produce glucose-6-phosphate; and, as a third reaction, the produced glucose-6-phosphate is reacted with an oxidized NAD compound in the presence of glucose-6-phosphate dehydrogenase to produce a reduced NAD compound; and a quantification section in which the reduced NAD compound produced in the reaction section is quantified.

<9> One embodiment of the invention is the ammonia quantification device according to <8>, wherein: in the reaction section, the reduced NAD compound is reacted with a coloring agent to produce a pigment, and in the quantification section, the produced pigment is quantified.

Effects of the Invention

According to one embodiment of the invention, a quantification method for ammonia, a quantification reagent kit, a test piece, and an ammonia quantification device, which enable highly sensitive quantification of ammonia without use of phosphoric acid as a reaction substrate can be provided.

MODE FOR CARRYING OUT THE INVENTION

Figure 1:
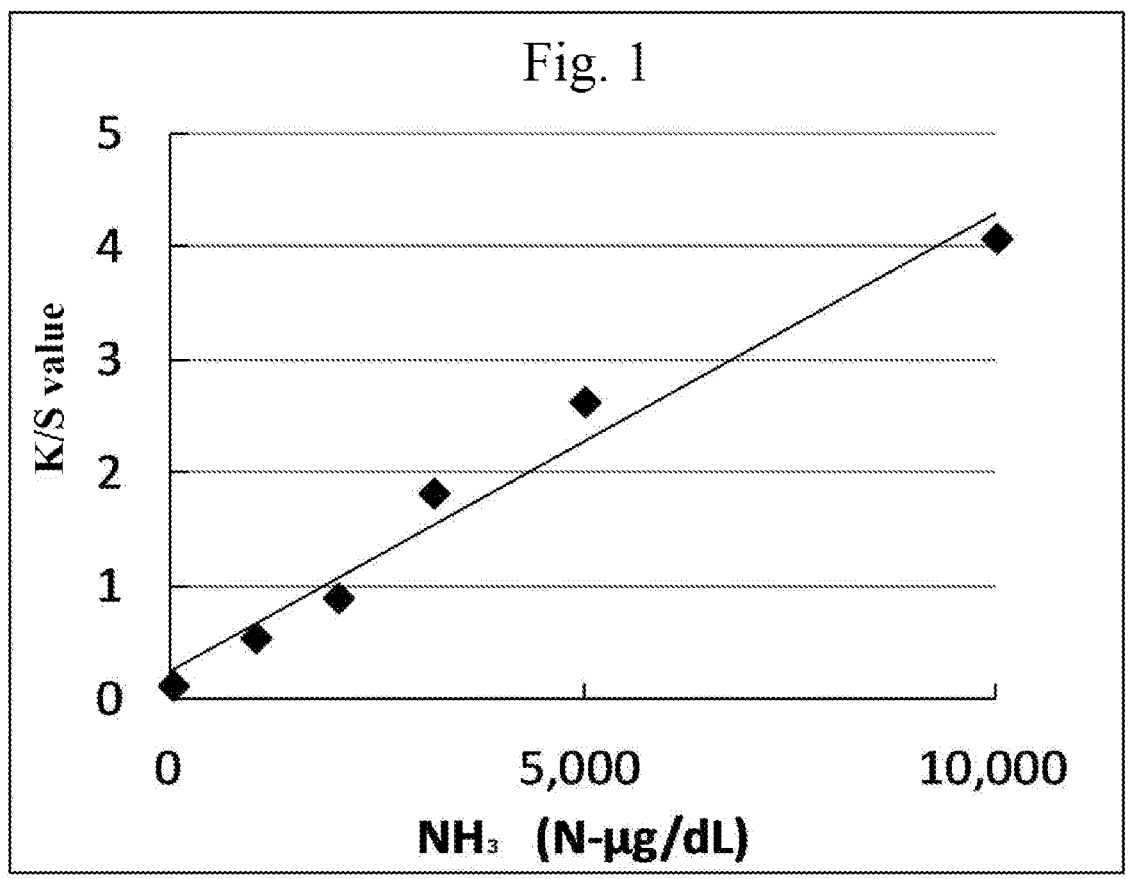
FIG. 1 is a graph showing the relationship between the amount of ammonia and the K/S value in Example 1.

The quantification method, the quantification reagent kit, the test piece, and the ammonia quantification device as one embodiment of the invention are described below.

In the present description, each numerical range expressed using "from . . . to . . . " means the range including the values described before and after "to" as the lower limit and the upper limit, respectively.

In the present description, "test liquid containing ammonia" means a test liquid containing at least one of ammonia or ammonium ion, and "ammonia concentration" and "amount of ammonia" mean the total concentration and the total amount, respectively, of ammonia and ammonium ion.

In the present description, each of the L-glutamic acid, phosphoric acid, and tetrazolium compound may be either a salt or an ion.

[Method of Quantifying Ammonia]

One embodiment of the invention is a method of quantifying ammonia, the method comprising: performing a first reaction in which a test liquid containing ammonia is reacted with ATP and L-glutamic acid in the presence of glutamine synthetase to produce ADP (adenosine diphosphate); performing a second reaction in which the produced ADP is reacted with glucose in the presence of ADP-dependent hexokinase to produce glucose-6-phosphate; performing a third reaction in which the produced glucose-6-phosphate is reacted with an oxidized NAD (nicotinamide adenine dinucleotide) compound in the presence of glucose-6-phosphate dehydrogenase to produce a reduced NAD compound; and quantifying the reduced NAD compound to quantify ammonia.

In the method of quantifying ammonia of the present embodiment, phosphoric acid produced by performing a first reaction in which a test liquid containing ammonia is reacted with ATP (adenosine triphosphate) and L-glutamic acid in the presence of glutamine synthetase is not used as a reaction substrate. Instead, ADP produced at the same time as the phosphoric acid is used as a reaction substrate. Thus, in the method of quantifying ammonia of the present embodiment, ammonia can be highly sensitively quantified without use of phosphoric acid as a reaction substrate.

Since the method of quantifying ammonia of the present embodiment is an end-point method in which ammonia is quantified by quantifying a final reaction product, control of the reaction can be simply carried out.

Since the method of quantifying ammonia of the present embodiment does not use an expensive reagent material such as NAD synthetase or phosphoenolpyruvate, but uses glucose, which is an inexpensive reagent material, quantification of ammonia can be carried out at low cost.

Since the method of quantifying ammonia of the present embodiment does not use dissolved oxygen in the reaction, the influence of dissolved oxygen can be avoided by, for example, carrying out the method of quantifying ammonia of the present embodiment in a closed system. Even in a case in which dissolved oxygen is contained in the test liquid, reagent, and/or the like, the reaction is less likely to be influenced by the dissolved oxygen since the quantification of ammonia is carried out in a reduction system that does not use an oxidase.

In the quantification method of the present embodiment, a test liquid containing ammonia is used. The test liquid is not limited as long as the test liquid contains ammonia. Examples of the test liquid include test liquids containing ammonia produced by an enzymatic reaction, and test liquids containing ammonia produced or released by a chemical reaction (for example, hydrolysis). More specific examples of the test liquid include blood, serum, urine, and saliva. In the quantification method of the present embodiment, the quantification of ammonia may be carried out by adding the later-described components to the test liquid to be analyzed, or the quantification of ammonia may be carried out by attaching the test liquid containing ammonia to filter paper or the like impregnated with the later-described components.

In the quantification method of the present embodiment, a test liquid containing ammonia is reacted with ATP and L-glutamic acid in the presence of glutamine synthetase to produce ADP (the first reaction). For example, a test liquid containing ammonia ($NH_3$) is reacted with ATP and L-glutamate in the presence of glutamine synthetase. As a result, ADP, orthophosphate, and L-glutamine are produced as shown in the following Reaction Formula (1).

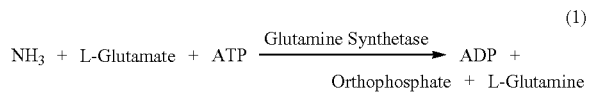

(1)

In the quantification method of the present embodiment, from the viewpoint of efficiently carrying out the synthesis reaction of ADP, it is preferred that the first reaction further include at least one of a magnesium ion ($Mg^{2+}$) or a manganese ion ($Mn^{2+}$), as a catalyst to produce the ADP.

In the quantification method of the present embodiment, the produced ADP is reacted with glucose in the presence of ADP-dependent hexokinase (a second reaction). For example, by performing a second reaction in which the produced ADP is reacted with D-glucose in the presence of ADP-dependent hexokinase (ADP-HK), glucose-6-phosphate (G6P) and AMP (adenosine monophosphate) are produced as shown in the following Reaction Formula (2).

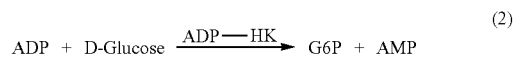

(2)

Subsequently, the produced glucose-6-phosphate is reacted with an oxidized NAD (nicotinamide adenine dinucleotide) compound in the presence of glucose-6-phosphate dehydrogenase (a third reaction). For example, by performing a third reaction in which the produced glucose-6-phosphate is reacted with an oxidized NAD ($NAD^+$) in the presence of glucose-6-phosphate dehydrogenase (G6PDH), reduced NAD (NADH) and D-glucono-1,5-lactone-6-phosphate (6-phosphogluconolactone) are produced as shown in the following Reaction Formula (3).

(3)

The NAD compound is not limited to the NAD (nicotinamide adenine dinucleotide) described above, and examples of the NAD compound also include thio-NAD (thionicotinamide adenine dinucleotide), NADP (nicotinamide adenine dinucleotide phosphate), and thio-NADP (thionicotinamide adenine dinucleotide phosphate).

As described above, by performing a third reaction in which glucose-6-phosphate is reacted with an oxidized NAD compound in the presence of glucose-6-phosphate dehydrogenase, a reduced NAD compound is produced. By quantifying the reduced NAD compound (for example, NADH), quantification of ammonia is carried out. Examples of such a method include a method in which ammonia is quantified by quantifying the reduced NAD compound itself, and a method in which ammonia is quantified by quantifying a pigment obtained by reacting the reduced NAD compound with a coloring agent. Examples of the former method include a method in which the electric current value observed upon generation of the reduced NAD compound is measured, and a method in which the amount of decrease in the absorbance (340 nm) derived from the reduced NAD compound caused by consumption of the reduced NAD compound is measured. Examples of the latter method include a method in which the amount of increase in the absorbance derived from the pigment caused by the production of the pigment is measured. Here, since the amount of decrease in the absorbance at a particular wavelength (340 nm) absorbed by the reduced NAD compound caused by consumption of the reduced NAD compound is in a proportional relationship with the ammonia concentration, and the amount of increase in the absorbance at a particular wavelength absorbed by the produced pigment is in a proportional relationship with the ammonia concentration, quantification of ammonia can be carried out by measuring the absorbance at the particular wavelength.

From the viewpoint of visual identification of the color tone, and from the viewpoint of obtaining a high measurement accuracy even in a case in which the ammonia concentration is low, a method in which ammonia is quantified by quantifying a pigment obtained by reacting the reduced NAD compound with a coloring agent is preferred.

Alternatively, the quantification of ammonia may be carried out by measuring the reflectance of a test paper obtained by attaching the produced pigment on filter paper or the like. For example, the quantification of ammonia may be carried out by attaching an ammonia solution to a test paper obtained by impregnating filter paper or the like with a liquid containing a substrate, enzyme, and the like to be used for the quantification of ammonia, and measuring the reflectance of the position on which the ammonia solution is attached.

In one example of the method of quantifying ammonia by quantification of a pigment, the produced NADH, which is a reduced NAD compound is reacted with a coloring agent tetrazolium violet (TV) in the presence of an electron carrier diaphorase (DI) (a fourth reaction). As a result, formazan dye is produced as shown in the following Reaction Formula (4), resulting in an increase in the absorbance at 560 nm.

(4)

The coloring agent is not limited as long as a pigment is produced by reaction with a reduced NAD compound, that is, as long as a pigment is produced by receiving an electron(s) from a reduced NAD compound. Examples of the coloring agent include tetrazolium compounds.

The tetrazolium compound is not limited as long as the compound has a tetrazole ring. The compound is preferably a compound having cyclic substituents at at least two positions in the tetrazole ring. The compound is more preferably a compound having cyclic substituents at at least three positions in the tetrazole ring.

In a case in which the tetrazolium compound has cyclic substituents at at least two positions in the tetrazole ring, the cyclic substituents are preferably positioned at 2-position and 3-position in the tetrazole ring. In a case in which the tetrazolium compound has cyclic substituents at at least three positions in the tetrazole ring, the cyclic substituents are preferably positioned at 2-position, 3-position, and 5-position in the tetrazole ring. Examples of the cyclic substituents include benzene rings that may have a substituent(s) (benzene ring-structure substituent), thienyl groups that may have a substituent(s), and thiazoyl groups that may have a substituent(s).

Examples of the tetrazolium compound having cyclic substituents at 2-position, 3-position, and 5-position in the tetrazole ring include 2-(4-iodophenyl)-3-(4-nitrophenyl)-5-(2,4-disulfophenyl)-2H-tetrazolium salt, 2-(4-iodophenyl)-3-(2,4-dinitrophenyl)-5-(2,4-disulfophenyl)-2H-tetrazolium salt, 2-(2-methoxy-4-nitrophenyl)-3-(4-nitrophenyl)-5-(2,4-disulfophenyl)-2H-tetrazolium salt, 2-(4-iodophenyl)-3-(4-nitrophenyl)-5-phenyl-2H-tetrazolium salt, 3,3'-(1,1'-biphenyl-4,4'-diyl)-bis(2,5-diphenyl)-2H-tetrazolium salt, 3,3'-[3,3'-dimethoxy-(1,1'-biphenyl)-4,4'-diyl]-bis[2-(4-nitrophenyl)-5-phenyl-2H-tetrazolium salt], 2,3-diphenyl-5-(4-chlorophenyl)tetrazolium salt, 2,5-diphenyl-3-(p-diphenyl)tetrazolium salt, 2,3-diphenyl-5-(p-diphenyl)tetrazolium salt, 2,5-diphenyl-3-(4-styrylphenyl)tetrazolium salt, 2,5-diphenyl-3-(m-tolyl)tetrazolium salt, and 2,5-diphenyl-3-(p-tolyl)tetrazolium salt.

The tetrazolium compound may also be a compound having benzene ring-structure substituents at two positions as well as another kind of cyclic substituent at one position in the tetrazole ring. Examples of such a compound include 2,3-diphenyl-5-(2-thienyl)tetrazolium salt, 2-benzothiazoyl-3-(4-carboxy-2-methoxyphenyl)-5-[4-(2-sulfoethylcarbamoyl)phenyl]-2H-tetrazolium salt, 2,2'-dibenzothiazoyl-5,5'-bis[4-di(2-sulfoethyl)carbamoylphenyl]-3,3'-(3,3'-dimethoxy-4,4'-biphenylene)ditetrazolium salt, and 3-(4,5-dimethyl-2-thiazoyl)-2,5-diphenyl-2H-tetrazolium salt.

The tetrazolium compound may also be a compound having benzene ring-structure substituents at two positions as well as an acyclic substituent at one position in the tetrazole ring. Examples of such a compound include 2,3-diphenyl-5-cyanotetrazolium salt, 2,3-diphenyl-5-carboxytetrazolium salt, 2,3-diphenyl-5-methyltetrazolium salt, and 2,3-diphenyl-5-ethyltetrazolium salt.

Among the tetrazolium compounds described above, compounds having three cyclic substituents are preferred. Compounds having three benzene ring-structure substituents together with an electron-withdrawing functional group(s) are more preferred. 2-(4-Iodophenyl)-3-(2,4-dinitrophenyl)-5-(2,4-disulfophenyl)-2H-tetrazolium salt is still more preferred.

Examples of the electron carrier include diaphorase, phenazine methosulfate, methoxyphenazine methosulfate, and dimethylaminobenzophenoxadinium chloride (Meldola Blue). Among the electron carriers, diaphorase is preferred.

In the quantification method of the present embodiment, the reaction temperature is preferably from 10° C. to 50° C., more preferably from 15° C. to 40° C., still more preferably from 20° C. to 30° C. The reaction time is preferably from 1 minute to 60 minutes, more preferably from 2 minutes to 30 minutes, still more preferably from 5 minutes to 15 minutes.

In the quantification method of the present embodiment, a buffer may be used for adjusting the pH of the test liquid containing ammonia to a pH suitable for enzymatic reaction (for example, to a pH of from 6.0 to 9.0). Examples of the pH of the buffer that may be used include pHs of preferably from 6.0 to 9.0, more preferably from 6.0 to 8.0. Examples of the buffer include Good's buffers such as N-tris(hydroxymethyl)methyl-2-aminoethanesulfonic acid (TES) and N,N-bis(2-hydroxyethyl)-2-aminoethanesulfonic acid (BES); phosphate buffer; imidazole acid buffer; Tris buffer; and glycine buffer.

In the quantification method of the present embodiment, a component(s) other than the components described above may be added to the test liquid containing ammonia, if necessary. Examples of the other component(s) include surfactants, antiseptics, and stabilizers.

[Quantification Reagent Kit and Test Piece]

One embodiment of the invention is a quantification reagent kit, comprising: a first reagent containing glucose; and a second reagent containing glutamine synthetase, ADP-dependent hexokinase, and glucose-6-phosphate dehydrogenase; wherein ATP, L-glutamic acid, and an oxidized NAD compound are each independently contained in at least one of the first reagent or the second reagent. The quantification reagent kit of the present embodiment is used for, for example, quantification of ammonia. The quantitative reagent kit of the present embodiment may be used for quantification of an object other than ammonia.

One embodiment of the invention is a test piece, comprising glucose, glutamine synthetase, ADP-dependent hexokinase, glucose-6-phosphate dehydrogenase, ATP, L-glutamic acid, and an oxidized NAD compound. The test piece of the present embodiment is used for, for example, quantification of ammonia. The test piece of the present embodiment may be used for quantification of an object other than ammonia.

Thus, with the quantification reagent kit and the test piece of the present embodiment, ammonia (the total of ammonia and ammonium ion) can be highly sensitively quantified without use of phosphoric acid as a reaction substrate.

In the quantification reagent kit of the present embodiment, ATP, L-glutamic acid, and oxidized NAD compound are preferably contained in the first reagent from the viewpoint of avoiding reaction of a substrate with an enzyme in a reagent.

In the quantification reagent kit of the present embodiment, the first reagent preferably further contains a coloring agent, and the second reagent preferably further contains an electron carrier from the viewpoint of quantifying a pigment obtained by reacting the reduced NAD compound with the coloring agent to quantify ammonia.

The first reagent and the second reagent in the quantification reagent kit, and the test piece of the present embodiment may contain the buffer and/or the other component described in the method of quantifying ammonia. Since the coloring agent and the electron carrier in the quantification reagent kit and the test piece of the present embodiment are the same as the coloring agent and the electron carrier described in the method of quantifying ammonia, description of the coloring agent and the electron carrier is omitted. The test piece of the present embodiment may be filter paper or the like, and/or may be filter paper or the like impregnated with the components.

[Ammonia Quantification Device]

One embodiment of the invention is an ammonia quantification device, performing a first reaction in which a test liquid containing ammonia is reacted with ATP and L-glutamic acid in the presence of glutamine synthetase to produce ADP; performing a second reaction in which the produced ADP is reacted with glucose in the presence of ADP-dependent hexokinase to produce glucose-6-phosphate; performing a third reaction in which the produced glucose-6-phosphate is reacted with an oxidized NAD compound in the presence of glucose-6-phosphate dehydrogenase to produce a reduced NAD compound; and quantifying the reduced NAD compound to quantify ammonia.

In the ammonia quantification device of the present embodiment, phosphoric acid produced by performing a first reaction in which a test liquid containing ammonia is reacted with ATP (adenosine triphosphate) and L-glutamic acid in the presence of glutamine synthetase is not used as a reaction substrate. Instead, ADP produced at the same time as the phosphoric acid is used as a reaction substrate. Thus, in the ammonia quantification device of the present embodiment, ammonia can be highly sensitively quantified without use of phosphoric acid as a reaction substrate.

Figure 2:
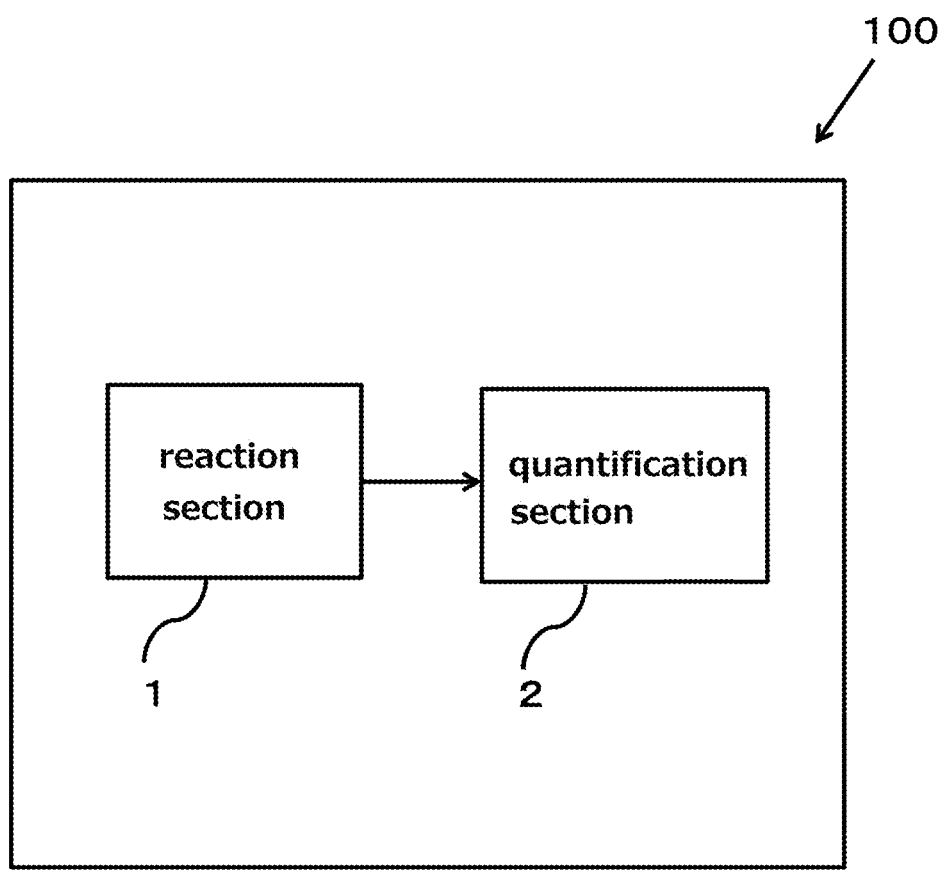
FIG. 2 is a schematic configuration diagram illustrating a quantification device 100 according to one embodiment of the invention.

Specific examples of the quantification device of the present embodiment are described below. Specific Example of the quantification device of the present embodiment is a quantification device including: a reaction section in which a test subject containing ammonia, glucose, glutamine synthetase, ADP-dependent hexokinase, glucose-6-phosphate dehydrogenase, ATP, L-glutamic acid, and an oxidized NAD compound, is arranged, wherein, in the test subject: as a first reaction, the ammonia is reacted with ATP and L-glutamic acid in the presence of glutamine synthetase to produce ADP; as a second reaction, the produced ADP is reacted with glucose in the presence of ADP-dependent hexokinase to produce glucose-6-phosphate; and, as a third reaction, the produced glucose-6-phosphate is reacted with an oxidized NAD compound in the presence of glucose-6-phosphate dehydrogenase to produce a reduced NAD compound; and a quantification section in which the reduced NAD compound is quantified. For example, as shown in FIG. 2, a quantification device 100 according to one embodiment of the invention may have at least a reaction section 1 for carrying out the reaction described above and a quantification section 2 for quantifying the reduced NAD compound produced by the reaction in the reaction section 1.

The quantification device of Specific Example has the reaction section described above. The reaction section has a constitution in which the test subject can be arranged. For example, the reaction section may have a constitution having the following: a place where a blood collection tube, urine collection tube, or the like storing a test liquid to be tested is arranged; a container storing a test liquid; filter paper which is impregnated with components to be used for the quantification of ammonia and to which a test liquid containing ammonia is attached; or the like.

The reaction section preferably has a constitution with which a reaction condition(s) (reaction temperature, pH of the test liquid, and/or the like) can be controlled such that the above reactions shown in the Reaction Formula (1) to the Reaction Formula (3) can be allowed to proceed efficiently.

The quantification device of Specific Example has the quantification section in which the reduced NAD compound produced in the reaction section is quantified. The quantification section has a constitution in which ammonia is quantified by quantifying the reduced NAD compound itself, and a constitution in which ammonia is quantified by quantifying a pigment obtained by reacting the reduced NAD compound with a coloring agent.

In a case in which the quantification section quantifies ammonia by quantifying the reduced NAD compound itself produced in the reaction section, it is preferred that the quantification section measure the electric current value observed upon generation of the reduced NAD compound, or the quantification section measures the amount of decrease in the absorbance (340 nm) derived from the reduced NAD compound caused by consumption of the reduced NAD compound.

In a case in which the quantification section quantifies ammonia by quantifying a pigment obtained by reacting the reduced NAD compound with a coloring agent, it is preferred that the reaction section have a constitution in which the reduced NAD compound is reacted with a coloring agent to produce a pigment, and the quantification section has a constitution in which the pigment produced in the reaction section is quantified. In this case, the quantification section preferably measures the amount of increase in the absorbance derived from the pigment caused by the production of the pigment.

In a case in which the quantification section quantifies ammonia by quantifying a pigment obtained by reacting the reduced NAD compound with a coloring agent, the quantification section may have a constitution in which the reflectance of a test paper attaching the pigment is measured.

The test subject containing ammonia to be analyzed in the quantification device of the present embodiment may also contain the catalyst, the buffer, and/or the other component described above in the method for quantifying ammonia.

The test subject containing ammonia and the components described above may be provided in advance, and the quantification device of the present embodiment may have a constitution in which the provided test subject is arranged in the reaction section.

The quantification device of the present embodiment may further have a storage section for storing the quantification reagent, for storing the first reagent and the second reagent, or for storing the components described above, and may have a constitution in which the reagents or components are supplied to the test liquid containing ammonia arranged in the reaction section. Alternatively, the quantification device of the present embodiment may have a constitution in which a test liquid containing ammonia is attached to filter paper or the like impregnated with the components to be used for the quantification of ammonia, arranged in the reaction section.

EXAMPLES

One embodiment of the invention is described below by way of Examples, but the invention is not limited to the Examples.

Example 1

The following Impregnation Liquid 1 and Impregnation Liquid 2 were prepared, and filter paper was provided.
<Impregnation Liquid 1>
TES—sodium hydroxide buffer (manufactured by Dojindo Molecular Technologies, Inc.; pH 7.0) 150 mmol/L
Sodium L-glutamate (manufactured by Nacalai Tesque, Inc.) 15 mmol/L
Oxidized nicotinamide adenine dinucleotide (manufactured by Roche) 15 mmol/L
Adenosine triphosphate dihydrate (manufactured by Roche) 15 mmol/L
Magnesium chloride hexahydrate 75 mmol/L
Glucose-6-phosphate dehydrogenase (manufactured by Toyobo Co., Ltd.) 80 U/mL
Diaphorase (manufactured by Asahi Kasei Corporation) 50 U/mL
ADP-dependent hexokinase (manufactured by Asahi Kasei Corporation) 40 U/mL
Glutamine synthetase (manufactured by Kikkoman Co., Ltd.) 45 U/mL
<Impregnation Liquid 2>
Glucose monohydrate (manufactured by Merck) 25 mmol/L
Tetrazolium violet (manufactured by Dojindo Molecular Technologies, Inc.) 15 mmol/L
<Filter Paper>
3MM HP (manufactured by Whatman)
Subsequently, the filter paper was impregnated with Impregnation Liquid 1, and then dried at 50° C. for 25 minutes. Subsequently, the filter paper impregnated with Impregnation Liquid 1 was impregnated with Impregnation Liquid 2, and then dried at 50° C. for 10 minutes to obtain a test piece. On the obtained test piece, aqueous ammonia solutions having the ammonia concentrations shown in FIG. 1 were spotted, and the test piece was left to stand at normal temperature for about 10 minutes, followed by reading the reflectance (560 nm) of the position on which each aqueous ammonia solution was spotted, and converting the reflectance to the following K/S value.

$K/S$ value=$(1-R)^2/2R$ (Kubelka-Munk equation; $R$ represents the reflectance)

As shown in FIG. 1, a favorable linear relationship could be obtained between the ammonia concentration and the K/S value at 560 nm.
Thus, the present Examples showed that highly sensitive quantification of ammonia is possible.

DESCRIPTION OF SYMBOLS

1. Reaction section
2. Quantification section
100. Quantification device

What is claimed is:
1. A test piece used for the method of quantifying ammonia, comprising a filter paper obtained by impregnating the filter paper with a first reagent and drying and subsequently impregnating the filter paper with a second reagent and drying,
wherein
the first reagent contains glutamine synthetase, ADP-dependent hexokinase and glucose-6-phosphate dehydrogenase,
the second reagent contains glucose, and
ATP contained in at least either one of the first reagent or the second reagent,
L-glutamic acid is contained in at least either one of the first reagent or the second reagent, and
the oxidized NAD compound is contained in at least either one of the first reagent or the second reagent.
2. The test piece used for the method of quantifying ammonia according to claim 1, wherein ATP, L-glutamic acid and an oxidized NAD compound are each independently contained in at least one of the first reagent or the second reagent.
3. The test piece used for the method of quantifying ammonia according to claim 1, wherein the first reagent further contains a coloring agent.
4. The test piece used for the method of quantifying ammonia according to claim 1, wherein the second reagent further contains an electron carrier.
5. An ammonia quantification device comprising the test piece of claim 1, comprising:
a reaction section having the test piece to which a test liquid containing ammonia is added,
wherein, in the test subject: as a first reaction, the ammonia is reacted with ATP and L-glutamic acid in the presence of glutamine synthetase to produce ADP; as a second reaction, the produced ADP is reacted with glucose in the presence of ADP-dependent hexokinase to produce glucose-6-phosphate; and, as a third reaction, the produced glucose-6-phosphate is reacted with an oxidized NAD compound in the presence of glucose-6-phosphate dehydrogenase to produce a reduced NAD compound; and
a quantification section in which the reduced NAD compound produced in the reaction section is quantified.
6. The ammonia quantification device according to claim 5, wherein:
in the reaction section, the reduced NAD compound is reacted with a coloring agent to produce a pigment, and
in the quantification section, the produced pigment is quantified.
7. A method of quantifying ammonia using the quantification reagent kit of claim 1, the method comprising:
performing a first reaction in which a test liquid containing ammonia is reacted with ATP and L-glutamic acid in the presence of glutamine synthetase to produce ADP;
performing a second reaction in which the produced ADP is reacted with glucose in the presence of ADP-dependent hexokinase to produce glucose-6-phosphate;
performing a third reaction in which the produced glucose-6-phosphate is reacted with an oxidized NAD compound in the presence of glucose-6-phosphate dehydrogenase to produce a reduced NAD compound; and
quantifying the reduced NAD compound to quantify ammonia.
8. The method of quantifying ammonia according to claim 7, wherein quantifying the reduced NAD compound to quantify ammonia is carried out by quantifying a pigment obtained by reacting the produced reduced NAD compound with a coloring agent.

9. The method of quantifying ammonia according to claim 7, wherein the first reaction further includes at least one of a magnesium ion ($Mg^{2+}$) or a manganese ion ($Mn^{2+}$), as a catalyst to produce the ADP.

10. The method of quantifying ammonia according to claim 8, wherein the first reaction further includes at least one of a magnesium ion ($Mg^{2+}$) or a manganese ion ($Mn^{2+}$), as a catalyst to produce the ADP.

* * * * *